United States Patent [19]

Bardy et al.

[11] Patent Number: 5,129,392
[45] Date of Patent: Jul. 14, 1992

[54] APPARATUS FOR AUTOMATICALLY INDUCING FIBRILLATION

[75] Inventors: Gust H. Bardy, Seattle, Wash.; Rahul Mehra, Stillwater, Minn.

[73] Assignee: Medtronic, Inc., Minneapolis, Minn.

[21] Appl. No.: 630,445

[22] Filed: Dec. 20, 1990

[51] Int. Cl.$^5$ .............................. A61N 1/39
[52] U.S. Cl. ..................... 128/419 D; 128/419 R
[58] Field of Search .................. 128/419 D, 419 R

[56] References Cited

U.S. PATENT DOCUMENTS

| | | | |
|---|---|---|---|
| 4,228,803 | 10/1980 | Rickards | 128/419 PG |
| 4,250,884 | 2/1981 | Hartlaub et al. | 128/419 PT |
| 4,253,466 | 3/1981 | Hartlaub et al. | 128/419 PG |
| 4,280,502 | 7/1981 | Baker, Jr. et al. | 128/419 PG |
| 4,305,396 | 12/1981 | Wittkampf et al. | 128/419 PG |
| 4,401,120 | 8/1983 | Hartlaub et al. | 128/419 PT |
| 4,548,209 | 10/1985 | Wielders et al. | 128/419 D |
| 4,550,370 | 10/1985 | Baker | 364/413 |
| 4,556,063 | 12/1985 | Thompson et al. | 128/419 PT |
| 4,693,253 | 9/1987 | Adams | 128/419 D |
| 4,766,900 | 8/1988 | Callaghan | 128/419 PG |
| 4,830,006 | 5/1989 | Haluska et al. | 128/419 PG |

FOREIGN PATENT DOCUMENTS 2811325  9/1979  Fed. Rep. of Germany ... 128/419 D
305892   7/1971  U.S.S.R. ..................... 128/419 D

OTHER PUBLICATIONS

"Electrical Defibrillation" by W. A. Tacker, Jr., M.D. Ph.D., et al., CRC Press Inc., Boca Raton, Fla., 1980.

Primary Examiner—William E. Kamm
Assistant Examiner—Scott M. Getzow
Attorney, Agent, or Firm—Reed A. Duthler; Harold R. Patton

[57] ABSTRACT

An automatic fibrillator for inclusion in an implantable defibrillator. Fibrillation induction takes place while the patient's heart is beating at a known rate, and the fibrillation inducing pulse is delivered at a time based on the expected or measured natural refractory period of the patient's heart, at the heart rate in effect during fibrillation induction. In its preferred embodiment, fibrillation induction takes place during overdrive pacing, and the timing of the pulse takes place using an overdrive pacing pulse as a time reference. The period between the pacing pulse and the fibrillation inducing pulse may be determined as a function of actual measurement of the patient's refractory period, either directory, or by means of measurement of the Q-T interval of the patient's heart.

52 Claims, 4 Drawing Sheets

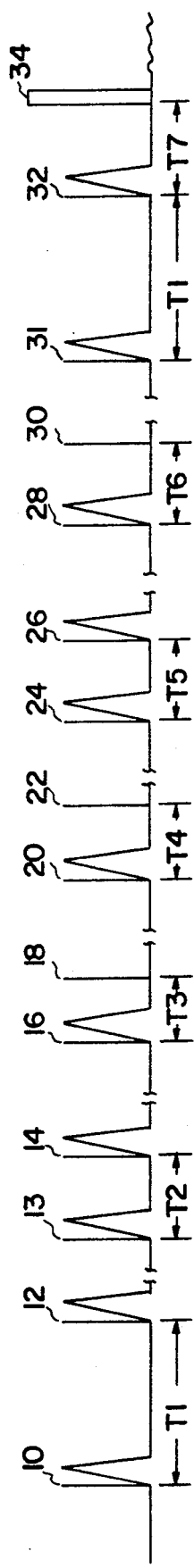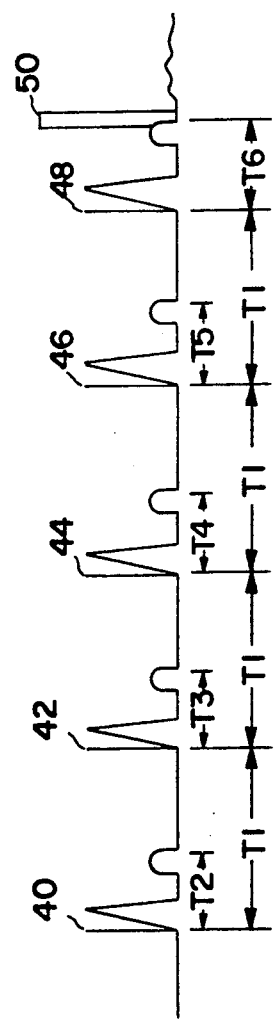
FIG.1a
FIG.1b

APPARATUS FOR AUTOMATICALLY INDUCING FIBRILLATION

BACKGROUND OF THE INVENTION

The present invention relates generally to medical stimulators and more specifically to implantable cardioverters and defibrillators.

When implanting an implantable defibrillator, it is desirable to test the device's operability to ensure that it is capable of reliably defibrillating the heart. In order to accomplish this, it is necessary to first induce fibrillation in the patient's heart, and then determine whether the implantable defibrillator is capable of terminating the induced fibrillation. Typically, a 60 cycle type fibrillator has been used in inducing fibrillation.

The inventors of the present application have determined that it would be desirable to incorporate the fibrillation induction function into an implantable defibrillator, to allow for a more fully automated testing regimen and to simplify the implantation procedure. However, incorporation of a 60 cycle defibrillator into an implantable device poses substantial technical difficulties. In any case, 60 cycle fibrillators frequently fail to induce fibrillation.

SUMMARY OF THE INVENTION

The present invention is directed toward providing an implantable fibrillator, preferably as part of an implantable cardioverter/defibrillator, which can reliably and automatically induce fibrillation. The inventors have determined that by accurately timing the delivery of a high voltage pulse, fibrillation can be reliably induced in most cases, using a single high voltage pulse. Fibrillation is induced immediately, so that the two second additional period of hemodynamic compromise which could occur during a 60 cycle fibrillation pulse is avoided. The inventors have further determined that appropriate timing of the high voltage pulse can be derived from a measurement of the patient's effective refractory periods measured directly or derived from a measurement of the patient's Q-T interval and that sufficient accuracy of the timing of the fibrillation inducing pulse is facilitated by using a pacing pulse delivered during overdrive pacing as a timing reference.

Typically, in implantable cardioverters and defibrillators, delivery of high voltage pulses for purposes of cardioversion or defibrillation is timed from sensing of natural ventricular contractions. However, the duration of the "R-wave" signal corresponding to an actual ventricular contraction is typically at least 50 ms., and the sense amplifiers typically used in implantable cardioverters and defibrillators are responsive to both variations in amplitude and frequency. As such, depending upon the configuration of the particular R-wave in question, the sense amplifier may detect the occurrence of the corresponding ventricular contraction at different points respective to the initiation of the R-wave. The inventors of the present application have determined that by timing the delivery of the high voltage pulse intended to induce fibrillation from an immediately preceding pacing pulse, a consistent timed relationship between the paced R-wave and the fibrillation pulse can be provided. This in turn allows for extremely accurate placement of the fibrillation pulse, relative to the refractory period of the patient's heart.

Further, the device of the present invention determines the refractory period of the heart based on paced contractions of the heart, paced at the same rate as the paced contraction immediately preceding delivery of the fibrillation pulse. This further enhances the accuracy of the timing of the delivery of the fibrillation pulse relative to the patient's present effective refractory period, and substantially increases the likelihood that a single pulse will be sufficient to fibrillate the heart.

Alternative embodiments of the invention forego the actual measurement of the patient's refractory period and instead employ a fixed delay based on known typical values for effective refractory periods at the rate of pacing in effect prior to delivery of the fibrillation pulse. Additional alternative embodiments may employ measurement of the effective refractory period of the patient's heart by means of measurement of the patient's Q-T interval and use the measured Q-T interval to control timing of fibrillation inducing pulses following spontaneous heartbeats.

BRIEF DESCRIPTION OF THE DRAWINGS

FIG. 1a is a simulated EKG strip illustrating the functioning of a first embodiment of the present invention.

FIG. 1b is a simulated EKG strip illustrating the functioning of a second embodiment of the present invention.

FIG. 3a is a flow chart illustrating the operation of the present invention when practiced in an embodiment corresponding to that illustrated in FIG. 1a.

DETAILED DESCRIPTION OF THE PREFERRED EMBODIMENTS

Figure 2:
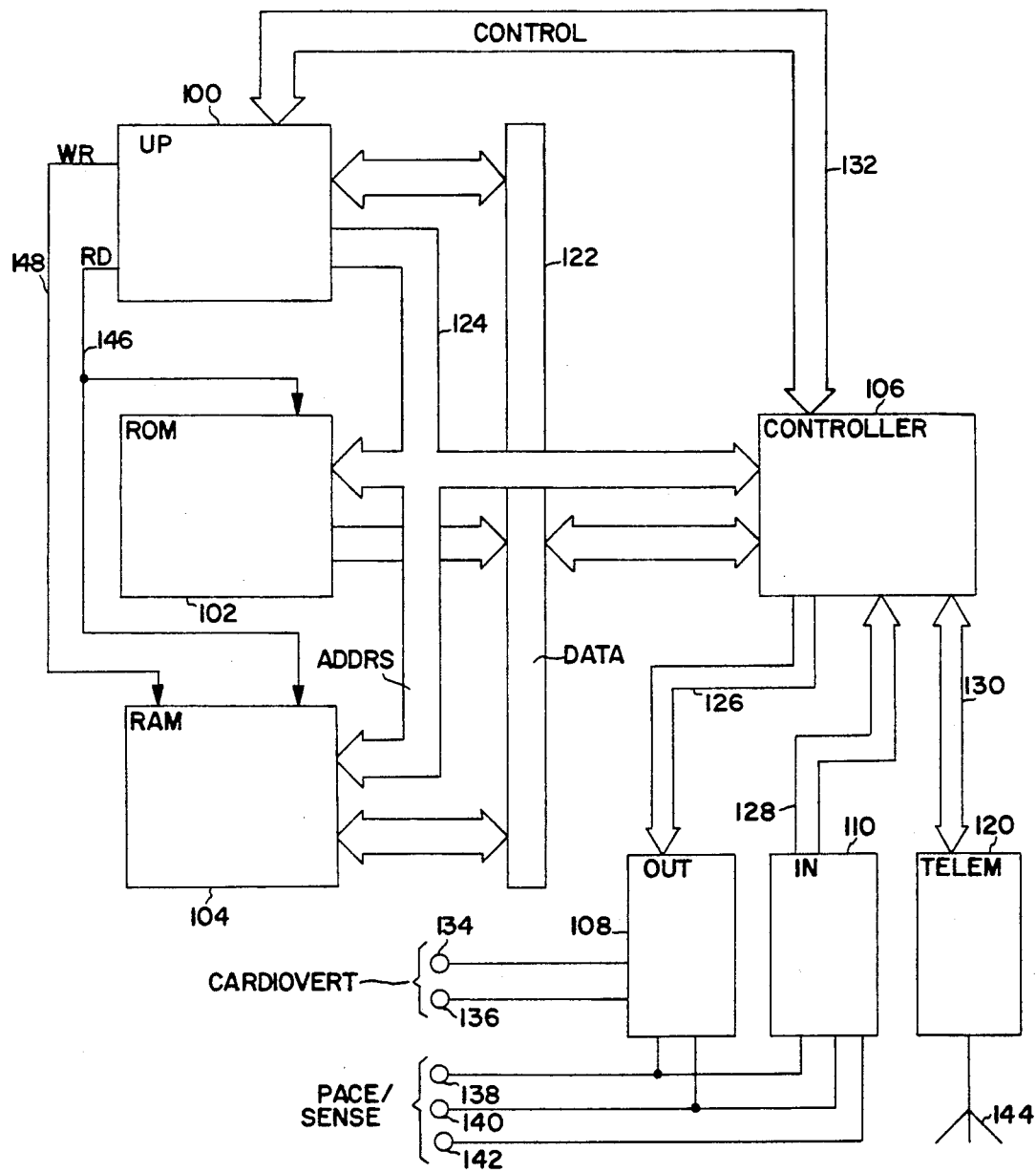
FIG. 2 is a functional block diagram of a device in which the present invention may be embodied.

FIG. 1a is a simulated EKG strip, illustrating the function of an implantable defibrillator incorporating the present invention. The EKG strip can be broken into two functional sections, with the preliminary portion of the EKG strip illustrating the method in which the device determines the patient's effective refractory period, and the later portion of the strip illustrating the timing and delivery of a high voltage pulse to induce fibrillation.

In its preferred embodiment, the fibrillation induction function is initiated by the physician by means of a programmer located exterior to the body which and provides programming signals to the implanted defibrillator. It is preferred that the fibrillation induction function be embodied in the form of a temporarily activatable feature, which is automatically disabled upon removal of or turn-off of the programmer, as disclosed in U.S. Pat. No. 4,253,466, issued to Hartlaub, incorporated herein by reference in its entirety. This is believed to provide a particularly useful safety function, which is especially desirable in the context of the fibrillation induction function of the present invention.

After the physician initiates the fibrillation induction function of the defibrillator, the device begins pacing the heart at a rate in excess of the patient's resting heart rate, so that it may overdrive the patient's heart. The rate at which this is accomplished is preferably selected by the physician, as a temporary parameter, as described in the above-cited Hartlaub patent. The amplitude of the pacing pulse is preferably twice the measured pacing threshold. It is contemplated that threshold measurement will be performed automatically, using the method and apparatus illustrated in U.S. Pat. No. 4,250,884, issued to Hartlaub et al., and incorporated herein by reference in its entirety. However, the invention may also be usefully practiced employing a fixed, high amplitude pacing pulse, e.g. a 5 volt, 1 ms pulse.

As illustrated, a rate of 150 beats per minute has been chosen so that the interval T1 separating pacing pulses 10 and 12 is approximately 400 ms. Overdrive pacing at this rate continues for eight pacing pulses, separated by T1 intervals. Only the first T1 interval is illustrated, in order to simplify the diagram. After the eighth such pacing pulse 13, a subsequent pacing pulse 14 is generated at an interval T2 thereafter. The duration of T2 is selected to be between a time interval TMIN measured from pacing pulse 13 during which it is expected that most patients' hearts will be refractory (e.g. TMIN equals 100 ms.), and a second time interval TMAX measured from pacing pulse 13, at the expiration of which it is expected that the patient's heart will not be refractory. TMAX may be selected by the physician, or may be set equal to a predetermined percentage of the overdrive pacing rate, e.g. 80 or 90%. As illustrated, TMAX is set at approximately 320 ms. T2 as illustrated is intermediate TMIN and TMAX, and, for purposes of the illustration in FIG. 1, is equal to TMIN plus TMAX divided by 2. As such, using the suggested values for TMIN and TMAX discussed above, T2 would be equal to 210 ms.

Following delivery of pacing pulse 14, the implanted device determines whether pacing pulse 14 has been successful in capturing the heart and causing a corresponding ventricular depolarization. While this function will be discussed in more detail below, for the purposes of the present invention it can be accomplished using any of a number of prior art methods for determining whether a pacing pulse has successfully captured the heart. For example, either the method disclosed in U.S. Pat. No. 4,305,396, issued to Wittkampf, et al, or the method disclosed in U.S. Pat. No. 4,766,900 issued to Callaghan, both of which are incorporated herein by reference in their entireties, may be used. However, any of the numerous alternative capture detection methods and devices known to the art may also be employed.

As illustrated in FIG. 1, pacing pulse 14 has been successful in capturing the heart. The implanted defibrillator again paces the heart at the overdrive pacing rate of 150 beats per minute, triggering generation of a eight pacing pulses separated by 400 ms. intervals. Following the eighth such pacing pulse 16, a subsequent pacing pulse 18 is generated, at an interval T3, which is intermediate between T2, known to be outside the refractory period of the heart, and TMIN, believed to be within the refractory period of the heart. As illustrated, the time interval T3 is selected to be 155 ms., equal to one-half of the sum of T2 and TMIN. As illustrated, this pulse is not successful in capturing the heart, indicating that pacing pulse 18 is within the refractory period of the heart.

Following generation of pacing pulse 18, the defibrillator returns to the overdrive pacing mode, and generates eight additional pacing pulses at 400 ms. intervals. In a manner similar to the calculation of the interval T3, a subsequent interval T4 is calculated separating the eighth such pacing pulse 20 from pacing pulse 22. In this case, because pacing pulse 18, which occurred at 155 ms. following the preceding paced contraction was found to be within the refractory period of the heart, pacing pulse 22 is generated at a time equal to one-half of the sum of T2 and T3. Pacing pulse 22 is thus generated 182.5 ms. after pacing pulse 20. As illustrated, pacing pulse 22 is unsuccessful in capturing the heart, indicating that it is within the refractory period of the patient's heart.

The defibrillator returns to the overdrive pacing mode, and generates eight subsequent overdrive pacing pulses at 400 ms. intervals. In a manner similar to the calculation of the time interval T4, a subsequent pacing pulses 26 and 30 are generated at time intervals T5 and T6 following pacing pulses 24 and 28. The duration of time interval T5 is equal to one-half of the sum of T4 and T2, i.e. approximately 196 ms. The duration of time interval T6 is equal to one-half of the sum of T4 and T5, i.e. approximately 190 ms. As illustrated, pacing pulse 26 is successful in capturing the heart and pulse 30 is not.

Because the time differential between T5, outside the refractory period of the heart and T6, within the refractory period of the heart is less than a predetermined value, for example 10 ms., the implantable defibrillator determines that T5 constitutes a sufficiently accurate measurement of the refractory interval of the heart. The value of T5 will be used to control the timing of the generation of a high voltage pulse to induce fibrillation. Following generation of pacing pulse 30, the defibrillator returns to the overdrive pacing mode, and generates overdrive pacing pulses 31 and 32 separated by 400 ms.

After generation of pacing pulse 32, the defibrillator begins timing of time interval T7, the interval between pacing pulse 32 and the generation of high voltage pulse 34, intended to induce fibrillation. The duration of time interval T7 is equal to the duration of time interval T5, plus a predetermined increment, typically on the order of 40 to 80 ms. The value of this incremental time interval should be selected by the physician, as should the amplitude of high voltage pulse 34. Typically, pulse 34 should have an amplitude of approximately 50 to 200 volts and a pulse width of 2 to 20 ms.

In the event that the high voltage pulse 34 is unsuccessful in inducing fibrillation, additional fibrillation inducing pulses may be delivered, employing a different incremental time interval added to the measured refractory period of the heart or employing a higher output fibrillation inducing pulse. In conjunction with repetition of the fibrillation induction function, the patient's refractory period may be remeasured or the fibrillation induction method represented by pulses 32 and 34 can immediately be repeated after verification that fibrillation has not been induced. In conjunction with repetition of the fibrillation induction function, either the time of delivery of the high voltage pulse or its amplitude may be scanned by regularly incrementing the interval added to the measured refractory period of the heart or by regularly incrementing the amplitude of the high voltage pulse.

As illustrated in FIG. 1, pulse 34 is successful in inducing fibrillation. At this point, the device exits the temporary fibrillation induction mode automatically, and returns to its underlying normal functionality, including operation of its tachycardia and fibrillation detection and terminating functions. While not discussed specifically in this application, the tachycardia and fibrillation detection and termination functions may correspond to any of those disclosed in previous patents relating to implantable cardioverter/defibrillators. For example, they may correspond to the detection and termination methodologies disclosed in U.S. Pat. No. 4,548,209, issued to Wielders, et al, U.S. Pat. No. 4,693,253, issued to Adams, U.S. Pat. No. or U.S. Pat. No. 4,830,006, issued to Haluska, et al, all of which are incorporated 5 herein by reference it their entireties. The present invention is believed to workable in the context of any of the numerous available fibrillation detection and termination methodology.

As can be seen from FIG. 1a, the delivery of the high voltage pulse 34 occurs when the heart is being paced at the same rate as it was paced during measurement of the refractory interval. As such, precise correspondence between the measured effective refractory period and the timing of the high voltage pulse is provided. As an alternative to the refractory period measurement method described above, measurement may be made according to the teaching of U.S. Pat. No. 4,280,502, issued to Baker et al, incorporated herein by reference in its entirety.

While actual measurement of the patient's refractory period is desirable, the invention may also be usefully practiced without actual measurement of the refractory period, allowing for substantial simplification of the apparatus embodying the invention. In such an embodiment, the duration of the interval separating the initial fibrillation pulse from the immediately preceding overdrive pacing pulse may be a fixed, predetermined interval based on the typical duration of patient's refractory periods when paced at the overdrive pacing rate. If the first fibrillation inducing pulse is unsuccessful, this fixed, predetermined interval may be incremented or the fibrillation inducing pulse level may be incremented as discussed above, until fibrillation is induced.

FIG. 1b illustrates an alternative embodiment of the present invention, in which the timing of the high voltage fibrillation inducing pulse is derived from a measurement of the Q-T interval. In FIG. 1, a series of pacing pulses 40, 42, 44, 46 and 48 are provided, generated at a rate of 150 beats per minute (400 ms. intervals). Following each pacing pulse, a measurement is made of the time interval between the pacing pulse and the peak of the T-wave or some other identifiable feature of the T-wave. In FIG. 1b these are illustrated as time intervals T2, T3, T4 and T5.

In a device according to the embodiment illustrated in FIG. 1b, time intervals T2 through T5 are averaged to produce an average Q-T interval. A predetermined interval of time, is added or subtracted from this average Q-T interval to provide interval T6, separating the final overdrive pacing pulse 48 from the high voltage, fibrillation inducing pulse 50. The duration of the time interval will depend upon the particular feature of the T-wave identified. Like the embodiment illustrated in FIG. 1a, accurate timing of the location of fibrillation inducing pulse 50 is possible because it is timed from the preceding ventricular pacing pulse 48. Again, delivery of the high voltage pulse 50 occurs when the heart is being paced at the same rate as it was paced during measurement of the Q-T interval. As such, precise correspondence between the depolarization induced by the pacing pulse 48 and the delivery of the high voltage pulse 50 is also provided.

While the disclosed embodiment of the invention discussed above measures intervals between pacing pulses and subsequent T-waves, the invention may also be usefully practiced by employing other methods of measuring time intervals between cardiac depolarizations (R-waves), including spontaneous depolarizations and subsequent T-waves. Further, In such embodiments, the interval separating the fibrillation inducing pulse from the preceding depolarization may in some cases be timed from some reference point with regard to the depolarization other than the pacing pulse.

FIG. 2 is a functional block diagram of an implantable cardioverter/defibrillator/pacemaker of the type in which the present invention may be practiced. The disclosed embodiment takes the form of a microprocessor controlled device. However, it is believed that the invention might usefully be practiced in other types of devices, including those employing dedicated digital circuitry, and perhaps even in devices comprised primarily of analog timing and control circuitry. As such, FIG. 2 should be considered exemplary, rather than limiting with regard to the scope of applications of the present invention.

The primary elements of the apparatus illustrated in FIG. 2 are a microprocessor 100, read only memory 102, random access memory 104, a digital controller 106, input and output amplifiers 110 and 108 respectively, and a telemetry/programming unit 120.

Read only memory 102 stores the basic programming for the device, including the primary instructions set defining the computations performed to derive the various timing intervals performed by the device. Random access memory 104 serves to store the values of variable control parameters, such as programmed pacing rate, programmed cardioversion and defibrillation intervals, pulse widths, pulse amplitudes, and so forth, which are programmed into the device by the physician. Random access memory also stores derived values, such as the intervals separating the overdrive pacing pulses 12, 16, 20, 24 and 28 (FIG. 1) from the subsequent refractory interval testing pulses 14, 18, 22 and 26, or from the subsequently generated high voltage pulse 30. Reading from random access memory 104 and read only memory 102 is controlled by RD-line 146. Writing to random access memory 104 is controlled by WR-line 148. In response to a signal on RD-line 146, the contents of random access memory 104 or read only memory 102 designated by the then present information on address bus 124 are placed on data bus 122. Similarly, in response to a signal on WR-line 148, information on data bus 122 is written into random access memory 104 at the address specified by the information on address bus 124.

Controller 106 performs all of the basic timing and control functions of the device. Controller 106 includes at least one programmable timing counter, initiated on ventricular contractions, paced or sensed, and timing out intervals thereafter. This timing counter is used to define the timing intervals referred to above, including the overdrive pacing interval ODINT, the intervals (TEST) separating the refractory interval testing pulses from immediately preceding overdrive pacing pulses, and the derived interval separating the delivery of the high voltage pulse from the immediately preceding overdrive pacing pulse. It is also anticipated that the controller 106 would also perform the basic timing functions of the pacing, cardioversion and tachycardia detection and termination routines performed by the device, as described in the above-cited prior art patents.

Controller 106 also triggers output pulses from output stage 108 as discussed below, and it generates interrupts on control bus 132 waking microprocessor 100 from its sleep state to allow it to perform the mathematical calculations referred to in conjunction with FIG. 1 above. Generally, it is anticipated that the controller 106 will generate interrupts to microprocessor 102 following either delivery of output pulses by output stage 108 or following detection of natural ventricular contractions by input stage 110, as discussed below. The time intervals which the timing counter in controller 106 counts are controlled by data stored in random access memory 104, applied to controller 106 via data bus 122.

Controller 106 also serves to control the capture detection function described in conjunction with FIG. 1 above. Initiation of the capture detection function is controlled by microprocessor 106, by means of control bus 132. Corresponding flags are generated by controller 106 indicating the success or failure of the pacing pulse to capture, and are placed on control bus 132 for use of the microprocessor in calculating the value of the TEST intervals, discussed above.

Controller 106 further serves to define the Q-T interval measurement function, performed in conjunction with the alternative embodiment discussed in conjunction with FIG. 1b. The Q-T interval measurement function can be performed as described in U.S. Pat. No. 4,228,803 issued to Rickards or in the above cited U.S. Pat. No. 4,644,954 issued to Wittkampf et al., both of which are incorporated herein by reference in their entireties. Basically, the controller defines a predetermined short blanking period, for example on the order of 70 or 80 ms., during and following the generation of a ventricular pacing pulse. The controller 106 then enables signals from electrodes 138 and 142 or from electrodes 140 and 142 to pass through. On detection of the peak amplitude, a signal from amplifier 110 is passed through to controller 106, which performs a measurement of Q-T interval used as described below to define the interval between an overdrive pacing pulse and the subsequent generation of a high voltage fibrillation inducing pulse.

Output stage 108 contains a high output pulse generator capable of generating cardioversion and defibrillation pulses. For purposes of the present invention, it is important that output stage 108 be also able to generate a high voltage pulse, of at least 100 volts, for use as a fibrillation inducing pulse in conjunction with the present invention. High output pulses, including cardioversion, defibrillation and fibrillation inducing pulses are applied to the patient's heart via electrodes 134 and 136, which are typically large surface area electrodes mounted on the heart, electrodes mounted in the heart, or some combination thereof. Any prior art implantable defibrillation electrode system made and used in conjunction with the present invention. Output circuit 108 is also coupled to electrodes 138 and 140 which are employed to accomplish ventricular bradycardia pacing. Electrode 138 is typically located on the distal end of a endocardial lead and is typically placed in the apex of the right ventricle. Electrode 140 is typically an indifferent electrode mounted on or adjacent to the housing of the implantable defibrillator. Output circuit 108 is controlled by control bus 122, which allows the controller 106 to determine the time, amplitude and pulse width of the pulse to be delivered and to determine which electrode pair will be employed to deliver the pulse.

Sensing of heart activity, both for normal sensing of ventricular contractions and for determining whether pacing pulses have successfully captured the heart is accomplished by input amplifier 110, coupled to electrodes 138, 140 and 142. Electrode 142 may be a ring electrode located on an endocardial lead, spaced from tip electrode 138, or it may be a far field electrode spaced between the heart and the indifferent electrode 140. Electrodes 138 and 140 are preferably employed to detect normal ventricular contractions. Electrodes 140 and 142 are preferably employed to detect whether or not delivered pacing pulses have captured the heart. A system for accomplishing these functions is disclosed in U.S. Pat. No. 4,766,900, issued to Callahan et al., and cited above.

Signals indicating the occurrences of natural ventricular contractions and paced ventricular contractions are provided to the controller 106 via bus 128. Controller 106 passes data indicative of the occurrence of such ventricular contractions to the microprocessor 100 via control bus 132, in the form of interrupts which serve to wake up microprocessor 100 so that it may perform any necessary calculations or updating of values stored in random access memory 104.

External control of the implanted defibrillator is accomplished via telemetry/control block 120, which allows communication between the implanted defibrillator and an external programmer. Radio communication is typically employed via antenna 124. Appropriate telemetry/programming systems are disclosed in U.S. Pat. No. 4,401,120, issued to Hartlaub et al, U.S. Pat. No. 4,556,063, issued to Thompson, et al, and U.S. Pat. No. 4,550,370, issued to Baker, all of which are incorporated herein by reference in their entireties. However, any conventional telemetry/programming circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130, for transmission to the external programmer.

Figure 3A:
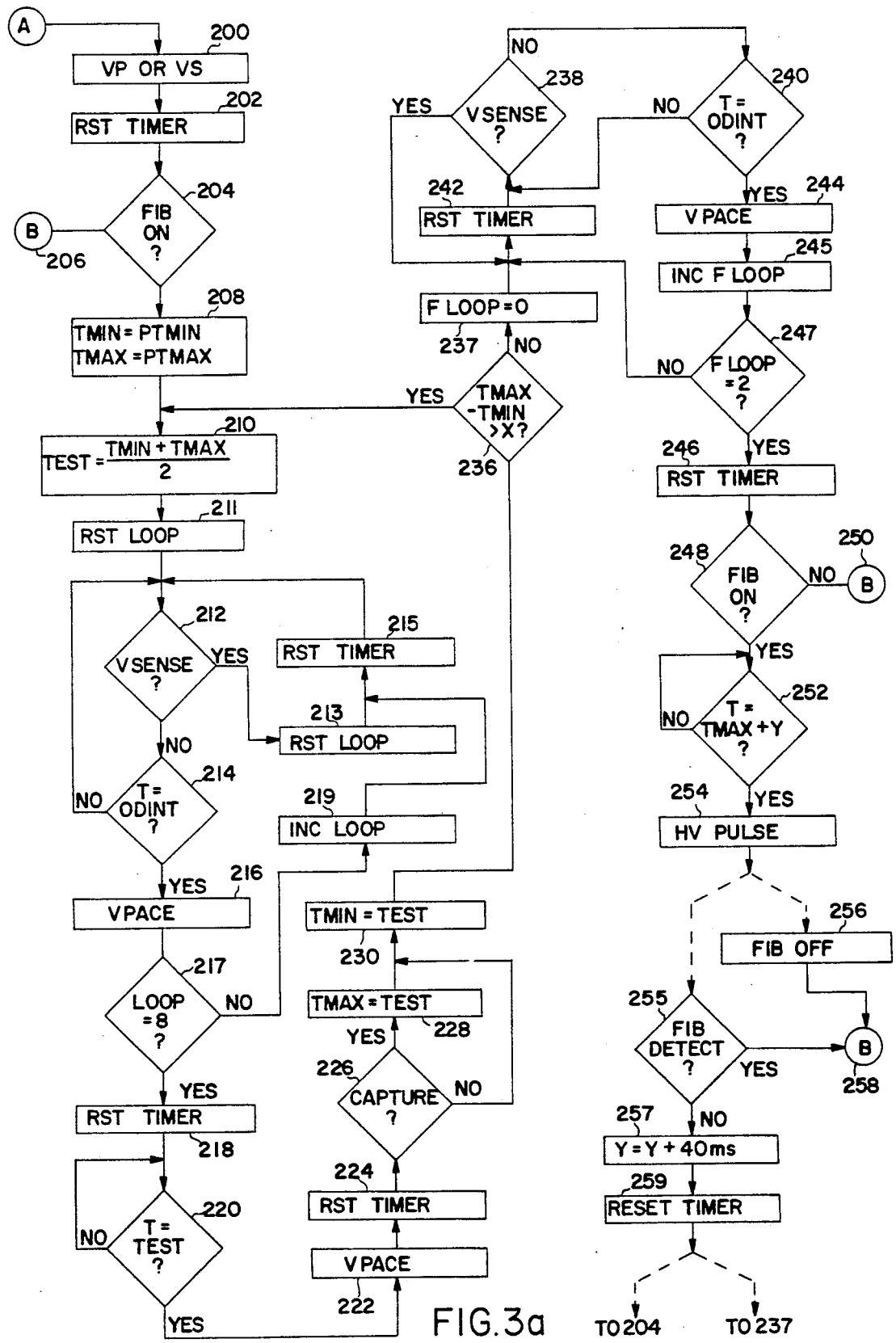

FIG. 3a is a functional flow chart illustrating the operation of the device shown in FIG. 2. This flow chart is intended to illustrate the functional operation of the device in an embodiment corresponding to FIG. 1a and should not be construed as reflective of a specific form of software or hardware necessary to practice the invention. It is believed that in the context of a microprocessor based embodiment of the present invention, the particular form of the software will be determined primarily by the microprocessor architecture chosen, and that providing appropriate software is well within the abilities of one with skill in the art, given the disclosure of the present application.

In the flow charts, "T" is the present value of the timing counter in controller 106. This counter is regularly incremented by clock pulses generated in controller 106. As used in the flow charts, this counter counts up from zero. However, it could as well take the form of a programmable jam-in down counter, in which zero represents time out of the interval specified. The timing counter is reset on delivery of pacing pulses, fibrillation inducing pulses, or on sensing of natural ventricular contractions.

FIG. 3a begins at point A which represents a point of interconnection between the software defining the main operating routine of the device, controlling pacing, cardioversion and defibrillation functions, and the software controlling the fibrillation inducing function of the device. For purposes of activating the fibrillation inducing function, the device must be operating in a standard, bradycardia pacing mode, and must not be involved in the delivery of any antitachyarrhythmia therapy.

After delivery of a ventricular pacing pulse or sensing of a natural contraction at 200, the microprocessor 100 is awakened from its sleep state by an interrupt generated by controller 106, and in turn resets the timing counter in controller 106, at 202. Microprocessor 100 then checks to determine whether the physician has activated the fibrillation inducing function of the defibrillator at 204. If a flag indicating that the fibrillation induction function has been selected is not present, the device continues to function normally, and continues with the main operational routine at point B, at 206.

In the event that the fibrillation induction function has been selected, the microprocessor initializes the operation of the function by setting the value of TMAX equal to PTMAX, a value entered by the physician, or calculated as a percentage of the overdrive pacing interval T1 and stored in random access memory 104. PTMAX corresponds to a time interval believed to be longer than the patient's effective refractory period. For purposes of FIG. 3a, it will be assumed that PTMAX equals 320 ms.

Similarly, at 208, the value TMIN is set equal to the value of PTMIN, stored in random access memory 104. PTMIN is preferably a value selected by the physician, or hard wired into the device, indicative of an interval known to be within the refractory period of essentially all patients. For example, 100 ms. is an appropriate value for PTMIN, and will be used in conjunction with the discussion of FIG. 3. At 210, the microprocessor 100 calculates the initial value of TEST, corresponding to the first test interval separating an overdrive pacing pulse from the next subsequent refractory interval testing pulse. At 211, the microprocessor 100 resets the loop count value to zero. The microprocessor then returns to the sleep state, allowing the timer in controller 106 to continue timing until either a ventricular contraction is sensed at 212, or the overdrive interval ODINT, also stored in random access memory 104, has timed out at 214.

In the event that a ventricular contraction is sensed, the loop counter is reset at 213 and the timer is reset at 215. In the event that it proves impractical to accomplish overdrive pacing, the physician may wish to reprogram the value of ODINT to a lesser value. If overdrive pacing is reliably accomplished, the refractory interval determination function should perform appropriately.

On expiration of ODINT, a ventricular pacing pulse is generated at 216, and controller 106 thereafter wakes microprocessor 100 from its sleep state via an interrupt. Microprocessor 100 checks to see if the loop count has been incremented to equal eight at 217. If not, the loop count is incremented to 219, the timer is reset at 215, and the microprocessor returns to the sleep state. If the loop count equals eight, indicating reliable overdrive pacing, the microprocessor 100 then resets the timer in controller 106 at 218, and performs whatever other necessary ministerial and control functions the device requires. The microprocessor 100 then returns to the sleep state, allowing the timer in controller 106 to time until the expiration of the TEST interval at 220, after which controller 106 triggers the generation of a ventricular pacing pulse at 222, and awakes microprocessor 100 from its sleep state via an interrupt signal. Microprocessor 100 then resets the timer in controller 106 at 224, and initiates the capture detect function at 226. In the event that the refractory interval testing pulse generates at 222 was successful in capturing the heart, the value of TMAX is replaced with the value of TEST at 228.

If the refractory period testing pulse generated at 222 was not successful in capturing the heart, the value of TMIN is replaced with the value of TEST at 230. The microprocessor then compares the current values of TMIN and TMAX to determine whether they differ more than a predetermined value "X".

Because the value of TMIN and TMAX at this point in the operation of the device represent a known value inside the refractory interval (the current value of TMIN) and a known value outside the refractory interval (TMAX) the comparison performed at 236 determines how closely the refractory interval of the patient has been bracketed. As discussed above in conjunction with FIG. 1, an appropriate value for "X" may be 10 or 15 ms. If the difference between TMIN and TMAX is greater than the value of X, the microprocessor recalculates a new value of TEST at 210, and reinitiates overdrive pacing and subsequent generation of a refractory interval testing pulse, as discussed above in conjunction with FIG. 1. This process continues until the difference between TMIN and TMAX at 236 is less than or equal to "X".

If TMAX-TMIN is less than "X" at 236, the microprocessor sets the value of the fibrillation loop count to zero at 237 and resets the timing counter in controller 106 at 242. The counter continues to time until either a ventricular contraction is sensed at 238 or the overdrive pacing ODINT is timed out at 240. In the event that a ventricular contraction is sensed at 238, the timer is reset at 242. Otherwise the timer continues to time until time out of the overdrive pacing interval at 240, at which point the controller triggers generation of an overdrive pacing pulse at 244, and wakens microprocessor 100 from its sleep state by means of an interrupt.

Microprocessor 100 then increments the fibrillation loop count at 245 and checks whether the count equals two. If the count is less than two, another cycle of overdrive pacing is initiated. Otherwise, the microprocessor resets the timer in controller 106 at 246, and again checks to be sure that fibrillation induction is still desired at 248. If fibrillation induction is no longer desired, the microprocessor re-enters the main routine at 250. If fibrillation induction is still desired, microprocessor 100 enables controller 106 to time out an interval equal to TMAX plus a predetermined increment "Y". On time out of the interval corresponding to TMAX plus "Y", at 252, a high voltage pulse is triggered at 254 by controller 106, and microprocessor 100 is reawakened.

Microprocessor 100 may thereafter generate an internal reset of the flag indicative that the fibrillation induction function has been selected at 256, and return to the main routine at 258, so that the device thereafter may detect the occurrence of fibrillation, if it has been successfully induced, and thereafter attempt to terminate it using the fibrillation termination methodologies available to the device. As such, both the fibrillation detection function of the device and the fibrillation termination function of the device are automatically tested.

It should be noted that the automatic return to the main routine at 256 requires the physician to specifically request repetition of the fibrillation induction function in the event that the first attempt at inducing fibrillation was unsuccessful. While the method illustrated in FIG. 3a will generally induce fibrillation successfully the first time, it is suggested that if fibrillation is not successfully induced the first time, the physician may wish to select a higher voltage level for the high voltage output pulse, or vary the value of the increment "Y" added to the detected refractory period of the patient's heart.

Alternatively, as discussed above, the fibrillation induction procedure may be automatically repeated by the defibrillator, with or without re-measuring the refractory period, with a different value for Y or a higher amplitude fibrillation inducing pulse. In such case, fibrillation detection would be performed at 255, with failure to induce fibrillation resulting in incrementing the value of "Y" at 257 and resetting the timer at 259. Re-entry to the fibrillation inducing procedure via block 204 will provide for re-measuring the refractory period, while re-entry at block 237 will provide for an immediate second attempt to induce fibrillation. An appropriate initial value for "Y" is 40 ms, with 80 ms being an appropriate incremented value.

As discussed above, it is possible to practice the invention without actual measurement of the refractory interval. In this case, the value of the interval separating the fibrillation inducing pulse from the immediately preceding pacing pulse may be based on the expected refractory interval at the rate of overdrive pacing, plus a predetermined increment.

Figure 3B:
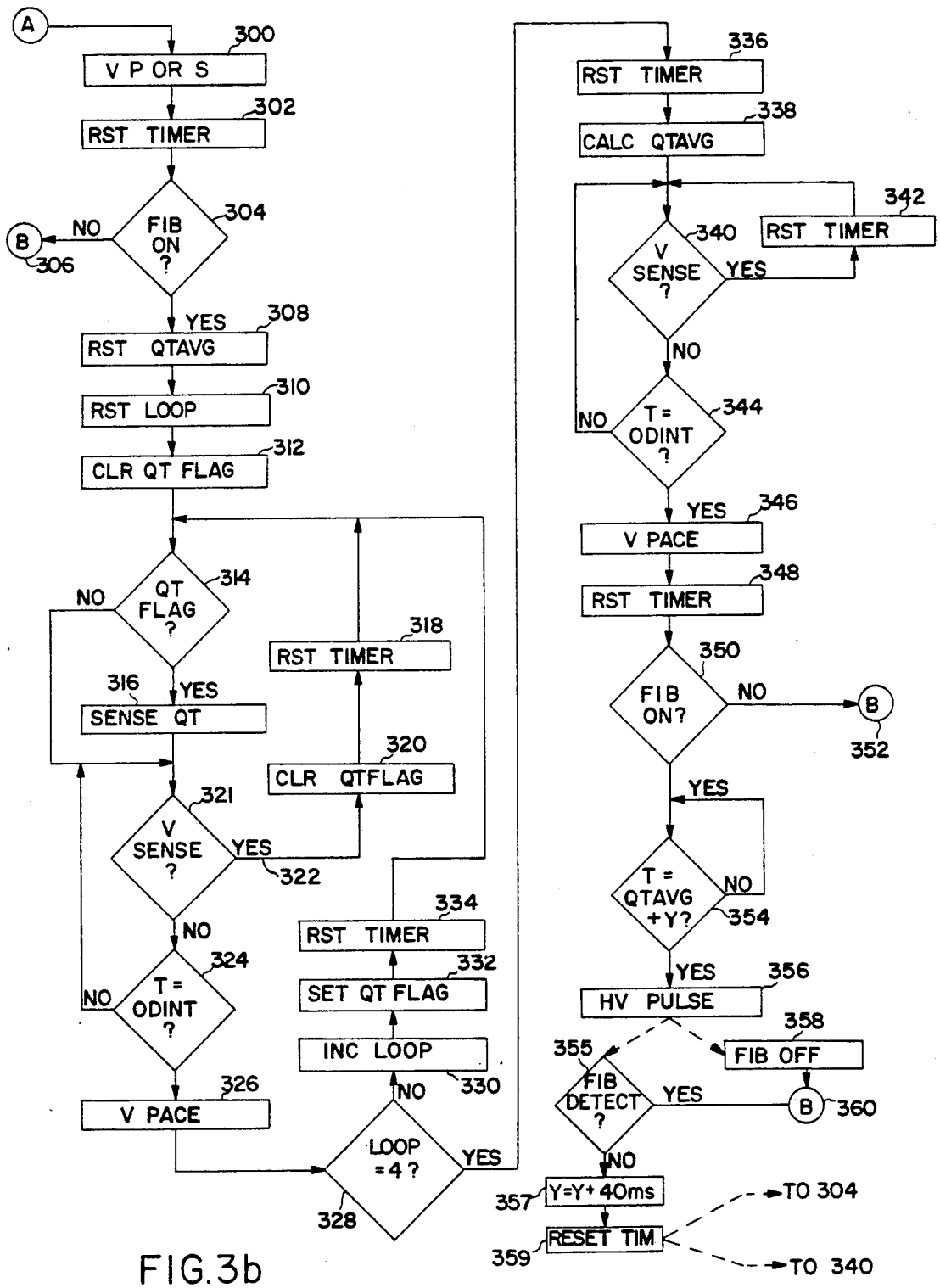
FIG. 3b is a flow chart illustrating the operation of the present invention when practiced in an embodiment corresponding to that illustrated in FIG. 1b.

FIG. 3b is a flow chart illustrating the operation of the device of FIG. 2, when configured to perform the fibrillation inducing function illustrated in FIG. 1b. In general, overall functioning of the device corresponds to the function of the device described in conjunction with FIG. 3a, with the microprocessor awakened only when necessary to perform calculations, modify functions or update information stored in the random access memory 104. For purposes of simplicity, only the functional operation of the device as reflected in FIG. 3b will be discussed in detail. As in the case of the implementation disclosed in FIG. 3d, on generation of a ventricular pacing pulse or sensing of a ventricular contraction at 300, the main timer is reset at 302, and the microprocessor 100 checks to see whether the fibrillation inducing function flag is set at 304. If not, the device returns to its main operational routine at 306. If the fibrillation inducing flag is on, the microprocessor 100 clears any stored information relating to previous average measured Q-T intervals at 308, resets the loop count stored in RAM 104 at 310, and clears the Q-T interval flag from controller 106 at 312. This initializes the Q-T measurement routine which will be used to determine the timing of the fibrillation inducing pulse.

The Q-T measurement routine begins at 314 where the Q-T flag status is checked. Initially, this flag will not be set, and the microprocessor 100 will return to the sleep state, until either a ventricular contraction is sensed at 321 or time out of the overdrive pacing interval ODINT at 324. On sensing of a ventricular contraction, the Q-T flag is cleared at 320, and the timer is reset at 318. On time out of the overdrive pacing interval, a ventricular pacing pulse is generated at 326, and the microprocessor is awakened from its sleep state. The microprocessor 100 checks to determine whether the loop count is equal to four at 328. If not, the loop count is incremented at 330, and the Q-T flag is set by controller 106 at 332, indicating delivery of a ventricular pacing pulse which will allow measurement of the Q-T interval thereafter. The timer is reset at 334, and the Q-T measurement routine is begun.

Because the Q-T flag is set at 314, the microprocessor enables the controller 106 to perform the Q-T measurement function. As discussed above, this measurement function may correspond to the Q-T measurement functions disclosed in the above-cited Rickards or Wittkampf patents. Similarly, it may correspond to any other known methodology for measuring the Q-T interval, or for measuring the interval between delivery of a pacing pulse and occurrence of a predetermined feature of the T-wave, such as peak slope, peak amplitude, or other detectable characteristic. After measuring the Q-T interval at 360, data indicative of the Q-T interval is provided to the microprocessor via data bus 122, and the microprocessor stores the measured Q-T interval in the random access memory 104. The microprocessor 100 then returns to the sleep state and waits for the occurrence of either a sensed ventricular contraction at 322 or time out of the overdrive pacing interval at 324. This process continues until the loop count equals four at 328. At this point, there will be four stored measured Q-T intervals, which is believed to be an adequate sample to calculate the average Q-T interval. However, a greater or lesser number of Q-T intervals might also be employed.

The routine for delivering the high voltage cardioversion pulse is initialized by resetting the timer at 336 and calculating the average of the stored Q-T intervals (Q-T AVG) at 338. The microprocessor 100 then returns to the sleep state and awaits time out of the overdrive interval at 344 or sensing of a ventricular contraction at 340. In the event that a ventricular contraction is sensed at 340, the timer will be reset at 342. This process continues until successful time out of an overdrive pacing interval at 344, causing generation of a ventricular pacing pulse at 346, which in turn awakens the microprocessor 100 thereafter. The microprocessor resets the timer at 348, and checks to determine whether the fibrillation flag is still set at 350. If not, the device exits to the main pacing/cardioversion routine at 352. If the fibrillation inducing flag is still set, the microprocessor enables the timer in controller 106 to time out a new interval equal to the Q-T average, plus a predetermined increment "Y", at 354. A typical value for "Y" would be about 40 ms., assuming that the Q-T intervals taken are intervals between the pacing pulse and the peak of the T-wave. After expiration of an interval equal to Q-T AVG plus "Y" at 354, a high voltage pulse is generated at 356, the fibrillation flag may be is set off at 358, and the device may then return to the main pacing and cardioversion routine at 360.

The invention may be usefully practiced in a device in which automated repetitive applications of incrementally increasing amplitude high voltage fibrillation inducing pulses and/or scanning of the value of the increment "Y" added to the determined refractory period of the patient might be performed. In such case, fibrillation detection would be performed at 355, with failure to induce fibrillation resulting in incrementing the value of "Y" at 357 and resetting the timer at 359. Re-entry to the fibrillation inducing procedure via block 304 will provide for re-measuring the Q-T interval, while re-entry at block 340 will provide for an immediate second attempt to induce fibrillation.

While the embodiment disclosed in FIG. 3b envisions that the measurement of Q-T intervals and the timing of the interval separating the fibrillation inducing pulse from the immediately preceding R-wave should be made using the pacing pulse as the timing reference for the R-wave, it may also be possible in some applications to use the sensed occurrence of the sensed depolarization signal as the timing reference for both functions.

While both disclosed embodiments of the present invention envision application of individual fibrillation inducing pulses, it is also believed that the invention might be practiced in conjunction with a fibrillation induction method which employs the application of pairs of high voltage pulse, timed based on the measured refractory period or Q-T interval of the patient, as an alternative to scanning the values for the time intervals separating fibrillation inducing pulses from preceding pacing pulses. As such, the disclosed embodiment should be considered exemplary rather than limiting with regard to the scope of the claims which follow.

In embodiments in which scanning of either the time interval separating delivery of the last overdrive pacing pulse and subsequent delivery of the high voltage cardioversion pulse is scanned, the scanning function is disclosed as automated entirely within the implanted device. However, control of the scanning function might also be provided by means of the external programmer, which performs the necessary incrementing and decrementing functions. Either approach is believed to be workable. It should be noted, however, that it is believed desirable that in all cases, the device should be configured so as to provide for cessation of the fibrillation inducing function on removal of the programming head, as a safety precaution.

In conjunction with the above disclosure, we claim:

1. A method of inducing fibrillation in a patient's heart, comprising:
   measuring the effective refractory period of said patient's heart while pacing said patient's heart at a predetermined rate;
   deriving a first time interval based on the measured refractory period of said patient's heart;
   delivering a fibrillation inducing pulse to said patient's heart at said first time interval following delivery of a pacing pulse to said patient's heart.

2. A method according to claim 1 wherein said derived first time interval comprises the measured refractory period of said patient's heart plus a predetermined second time interval.

3. A method of inducing fibrillation in a patient's heart, comprising:
   measuring a time related characteristic of the T-waves of said patient's heart following cardiac pacing pulses delivered at a predetermined rate;
   deriving a first time interval based on said measured characteristic of said patient's T-waves;
   delivering a fibrillation inducing pulse to said patient's heart at said first time interval following delivery of a pacing pulse to said patient's heart.

4. A method according to claim 1 or 3, wherein said fibrillation inducing pulse is delivered following a pacing pulse which follows an immediately preceding pacing pulse by an interval corresponding to said predetermined rate.

5. A method according to claim 3 wherein said time related characteristic is the Q-T interval of said patient's heart.

6. A method according to claim 5 wherein said derived first time interval comprises the measured Q-T interval of said patient's heart plus a predetermined second time interval.

7. A method according to claim 6 or claim 2 wherein said second time interval is a fixed time interval.

8. A method according to claim 1 or claim 3 further comprising the step of monitoring said patient's heart following delivery of said fibrillation inducing pulse to determine whether fibrillation is induced.

9. A method according to claim 8 further comprising the step of repeating the step of delivery of said fibrillation inducing pulse until fibrillation is induced.

10. A method according to claim 9 comprising the step of increasing the amplitude of said fibrillation inducing pulse in the event that fibrillation is not induced by delivery of a fibrillation inducing pulse.

11. A method according to claim 9 comprising the step of varying the duration of said first time interval in the event that fibrillation is not induced by delivery of a fibrillation inducing pulse.

12. An automatic fibrillator, comprising:
    means for generating pacing pulses to pace a patient's heart at a predetermined rate;
    means for measuring the refractory period of said patient's heart while pacing said patient's heart at said predetermined rate;
    means for deriving a first time interval based on the measured refractory period of said patient's heart; and
    means for delivering a fibrillation inducing pulse to said patient's heart at said first interval following generation of one of said pacing pulses.

13. A fibrillator according to claim 12 wherein said deriving means comprises means for deriving a first interval equal to said measured refractory period of said patient's heart plus a predetermined second time interval.

14. A fibrillator according to claim 13 wherein said predetermined second time interval is fixed in duration.

15. An automatic fibrillator, comprising:
    means for generating pacing pulses to pace a patient's heart art a predetermined rate;
    means for measuring a time related characteristic of the T-waves of said patient's heart;
    means for deriving a first time interval based on the measurement of said time related characteristic;
    means for delivering a fibrillation inducing pulse at said first time interval following the generation of one of said pacing pulses.

16. A fibrillator according to claim 12 or 15 wherein said delivering means comprises means for delivering said fibrillation inducing pulse following the generation of a first one of said pacing pulses preceded by a second one of said pacing pulses, said first and second pulses generated at said predetermined rate.

17. A fibrillator according to claim 15 wherein said measuring means comprises means for measuring the patient's Q-T interval.

18. A fibrillator according to claim 17 wherein said deriving means comprises means for deriving a first time interval equal to said measured Q-T interval plus a predetermined second time interval.

19. A fibrillator according to claim 12 or 15 further comprising means for monitoring said patient's heart following delivery of said fibrillating pulse to determine whether fibrillation is induced.

20. A fibrillator according to claim 19 further comprising means for repeatedly delivering fibrillation inducing pulses until fibrillation is induced.

21. A fibrillator according to claim 20 further comprising means to vary the duration of said first time interval in the event that fibrillation is not induced by the delivery of a fibrillation inducing pulse.

22. A fibrillator according to claim 20 further comprising means to vary the amplitude of fibrillation inducing pulses in the event that fibrillation is not induced by delivery of a fibrillation inducing pulse.

23. A method of inducing fibrillation in a patient's heart, comprising:
    pacing said patient's heart at a predetermined rate;
    defining a first time interval based on the refractory period of said patient's heart when paced at said predetermined rate;
    delivering a fibrillation inducing pulse to said patient's heart at said first time interval following delivery of a pacing pulse at said predetermined rate to said patient's heart.

24. A method according to claim 23 further comprising the step of measuring the refractory period of said patient's heart while pacing said patient's heart at said predetermined rate and wherein said first time interval comprises the measured refractory period of said patient's heart plus a predetermined second time interval.

25. A method according to claim 24 wherein said second time interval is a fixed time interval.

26. A method of inducing fibrillation in a patient's heart, comprising:
    measuring a time related characteristic of the T-waves of said patient's heart following cardiac depolarizations;
    deriving a first time interval based on said measured characteristic of said patient's T-waves;
    delivering a fibrillation inducing pulse to said patient's heart following a depolarization of said patient's heart, at the expiration of said first time interval.

27. A method according to claim 26 wherein said time related characteristic is the Q-T interval of said patient's heart.

28. A method according to claim 27 wherein said derived first time interval comprises the measured Q-T interval of said patient's heart adjusted by a predetermined increment.

29. A method according to claim 26 further comprising the step of inducing a cardiac depolarization by delivering a cardiac pacing pulse and wherein said step of delivering a fibrillation inducing pulse comprises delivering said fibrillation inducing pulse at the expiration of said first interval following delivery of said cardiac pacing pulse.

30. A method according to claim 29 wherein said step of measuring said time related characteristic comprises measuring the interval between delivery of cardiac pacing pulses and the occurrence of a repeatably detectable characteristic of the T-waves of said patient's heart.

31. A method according to claim 23 or claim 26 further comprising the step of monitoring said patient's heart following delivery of said fibrillation inducing pulse to determine whether fibrillation is induced.

32. A method according to claim 31 further comprising the step of repeating the step of delivery of said fibrillation inducing pulse until fibrillation is induced.

33. A method according to claim 32 comprising the step of varying the duration of said first time interval in the event that fibrillation is not induced by delivery of a fibrillation inducing pulse.

34. A method according to claim 32 comprising the step of increasing the amplitude of said fibrillation inducing pulse in the event that fibrillation is not induced by delivery of a fibrillation inducing pulse.

35. An automatic fibrillator, comprising:
    means for generating pacing pulses to pace a patient's heart at a predetermined rate;
    means for defining a first time interval based on the refractory period of said patient's heart when paced at said predetermined rate; and
    means for delivering a fibrillation inducing pulse to said patient's heart at said first interval following generation of one of said pacing pulses at said predetermined rate.

36. A fibrillator according to claim 35 further comprising means for measuring the refractory period of said patient's heart while pacing said patient's heart at said predetermined rate and wherein said first time interval comprises the measured refractory period of said patient's heart plus a predetermined second time interval.

37. A fibrillator according to claim 36 wherein said second time interval is a fixed time interval.

38. An automatic fibrillator, comprising:
    means for measuring a time related characteristic of the T-waves of said patient's heart following cardiac depolarizations;
    means for deriving a first time interval based on the measurement of said time related characteristic;
    means for delivering a fibrillation inducing pulse following a cardiac depolarization, at the expiration of said first time interval.

39. A fibrillator according to claim 38 wherein said time related characteristic is the Q-T interval of said patient'heart.

40. A fibrillator according to claim 39 wherein said derived first time interval comprises the measured Q-T interval of said patient's heart adjusted by a predetermined increment.

41. A fibrillator according to claim 38 further comprising means for inducing a cardiac depolarization by delivering a cardiac pacing pulse and wherein said means for delivering a fibrillation inducing pulse comprises means for delivering said fibrillation inducing pulse at the expiration of said first interval following delivery of said cardiac pacing pulse.

42. A fibrillator according to claim 41 wherein said means for measuring said time related characteristic comprises means for measuring the interval between delivery of said cardiac pacing pulses and the occurrence of a repeatedly detectable characteristic of the T-waves of said patient'heart.

43. A fibrillator according to claim 35 or 38 further comprising means for monitoring said patient's heart following delivery of said fibrillation inducing pulse to determine whether fibrillation is induced.

44. A fibrillator according to claim 43 further comprising means for repeating the step of delivery of said fibrillation inducing pulse until fibrillation is induced.

45. A fibrillator according to claim 44 comprising means for varying the duration of said first time interval in the event that fibrillation is not induced by delivery of a fibrillation inducing pulse.

46. A fibrillator according to claim 44 comprising means for increasing the amplitude of said fibrillation inducing pulse in the event that fibrillation is not induced by delivery of a fibrillation inducing pulse.

47. A method of inducing fibrillation in a patient's heart, comprising:

measuring the effective refractory period from depolarizations of said patient's heart while said patient's heart is beating at a known rate;

deriving a first time interval based on the measured refractory period of said patient's heart;

delivering a fibrillation inducing pulse to said patient's heart at said first time interval following a depolarization of said patient's heart while said patient'heart is beating at said known rate.

48. A method according to claim 47 wherein said measuring step comprises pacing said patient's heart at said known rate.

49. A method according to claim 47 wherein said measuring step comprises measuring the Q-T interval of said patient's heart.

50. An automatic fibrillator, comprising:

means for measuring the refractory period following depolarizations of said patient'heart while said patient's heart beats at a known rate;

means for deriving a first time interval based on the measured refractory period of said patient's heart;

means for delivering a fibrillation inducing pulse to said patient's heart at said first interval following a depolarization of said patient's heart while said patient's heart beats at said known rate.

51. A fibrillator according to claim 50 wherein said measuring means comprises means for pacing said patient's heart at said known rate while measuring said refractory period.

52. A method according to claim 50 wherein said measuring means comprises means for measuring the Q-T interval of said patient's heart.

* * * * *